(12) United States Patent
Mertelmeier

(10) Patent No.: US 7,313,225 B2
(45) Date of Patent: Dec. 25, 2007

(54) METHOD AND APPARATUS FOR GENERATING OF A DIGITAL X-RAY IMAGE

(75) Inventor: Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/435,206

(22) Filed: May 15, 2006

(65) Prior Publication Data
US 2006/0262904 A1 Nov. 23, 2006

(30) Foreign Application Priority Data
May 17, 2005 (DE) .................. 10 2005 022 544

(51) Int. Cl.
*H05G 1/58* (2006.01)
(52) U.S. Cl. .................. 378/116; 378/62; 378/19
(58) Field of Classification Search .............. 378/62, 378/54, 98.8, 95, 98.12, 4–27, 98.11, 115, 378/116, 901; 382/130–132
See application file for complete search history.

(56) References Cited

U.S. PATENT DOCUMENTS

| 6,196,715 B1* | 3/2001 | Nambu et al. .............. 378/197 |
| 2003/0095631 A1* | 5/2003 | Rosner ..................... 378/98.12 |
| 2005/0110748 A1 | 5/2005 | Boeing et al. |
| 2005/0135664 A1* | 6/2005 | Kaufhold et al. ........... 382/131 |
| 2006/0110064 A1* | 5/2006 | Battle et al. ................ 382/274 |

* cited by examiner

*Primary Examiner*—Courtney Thomas
(74) *Attorney, Agent, or Firm*—Schiff Hardin LLP

(57) ABSTRACT

In a method and an apparatus for acquisition of a digital x-ray image of an examination subject with a digital x-ray receiver, the digital x-ray image being composed of a number of individual images acquired in temporal succession and overlapping one another at least in one diagnostically-relevant subject region, at least one intermediate image composed of a number of individual images is evaluated to control at least one acquisition parameter used to generate the x-ray image. For the acquisition of digital x-ray images, an exposure control without exposure of the patient to an additional radiation dose is possible.

14 Claims, 2 Drawing Sheets

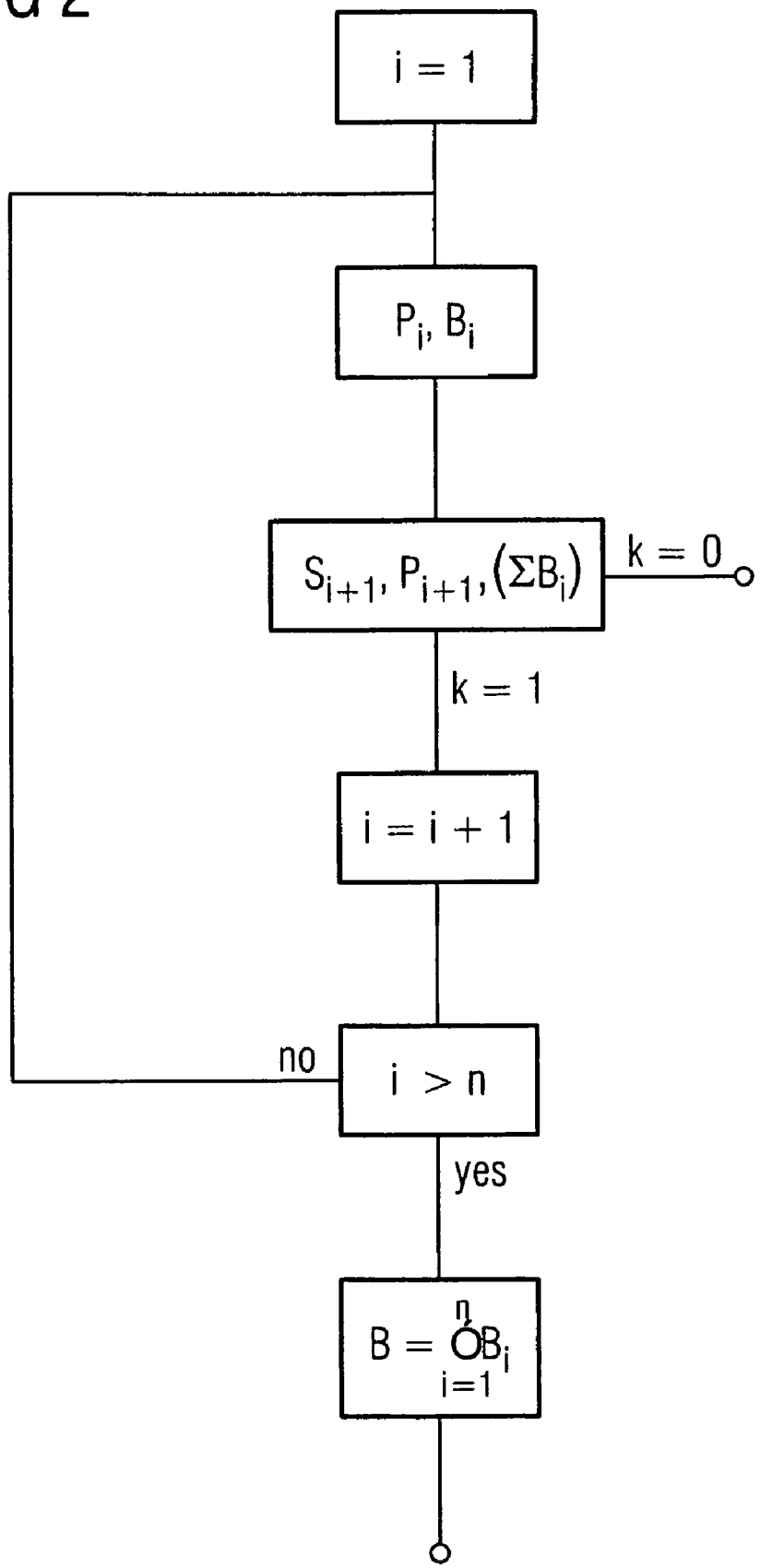

METHOD AND APPARATUS FOR GENERATING OF A DIGITAL X-RAY IMAGE

BACKGROUND OF THE INVENTION

1. Field of the Invention

The present invention concerns a method and an apparatus for generating a digital x-ray image of an examination subject.

2. Description of the Prior Art

In the acquisition of an x-ray image of an examination subject, for example in mammography, it must be ensured that the acquisition parameters (in particular the exposure time) are set correctly in order to achieve an image quality suitable for diagnostic evaluation. In order to limit the radiation exposure of the irradiated region of the examination subject to the diagnostically-required minimum, it is intended to already correctly set the acquisition parameters in the first acquisition. For this purpose, in the prior art an automatic exposure (AEC, automatic exposure control) is used. For mammography, a number of solid-state detectors are arranged behind the x-ray film (viewed in the propagation direction of the x-rays) that measure the intensity of the x-rays transmitted through the x-ray film. The output signal is used to control the acquisition parameters (for example exposure time, operating voltage of the x-ray tube, tube current, anode filter combination).

Due to the higher absorption of the solid-state detector array used in the acquisition of digital x-ray images, such a procedure is not possible for the acquisition of digital x-ray images. In digital x-ray acquisition, the acquisition parameters suitable for control of the exposure are determined in a pre-shot with a reduced radiation dose, in which a number of individual detectors of the matrix-like solid-state detector array are respectively combined into a measurement field and an average intensity within this measurement field is determined. In this manner, a number of measurement fields (for example 600 measurement fields) are generated in which the average brightness is respectively determined. The acquisition parameters (in particular the exposure time for the following acquisition of the digital x-ray image) are derived from these 600 average values. Due to this averaging, the measurement data acquired in the pre-shot cannot be diagnostically utilized and thus represent an additional radiation exposure for the patient.

SUMMARY OF THE INVENTION

An object of the present invention is to provide a method for the acquisition of a digital x-ray image of an examination subject with a digital x-ray receiver, wherein the disadvantage described above is avoided. A further object is to provide an apparatus for implementation of the method.

The above object is achieved according to the invention by a method wherein the digital x-ray image is formed by a number of individual images acquired in temporal succession and that overlap in at least one diagnostically-relevant subject region, and wherein at least one intermediate image formed by a number of individual images is evaluated to control at least one acquisition parameter used for generation of the following individual image. Since an intermediate image is evaluated to control the acquisition parameter. The intermediate image is composed of a number of existing individual images with maximum possible spatial resolution corresponding to the digital x-ray detector that is used (for example the first individual image or a number of individual images that are used for generation of the finished x-ray image. A pre-shot, that cannot be diagnostically utilized and that incurs an unnecessary dose exposure, is no longer necessary.

The term "acquisition parameters," as used herein encompasses all quantities that establish the operation of the x-ray tube. These are primarily the exposure time as well as operating parameters of the x-ray tube such as, for example, anode-filter combinations, high voltage or tube current as well as controllable diaphragms (if present) with which the image field can be delimited.

The individual images overlap one another at least in one diagnostically-relevant subject region, and the image fields respectively reproduced in the individual images can be identical. In principle, it is also possible after evaluation of one or more individual images to delimit the image field to the diagnostically-necessary dimensions using an adjustable collimator.

The intermediate image (or images can be a single image or can be the first acquired individual images or an intermediate image composed of a series of successive individual images) also can be diagnostically utilized, with other acquisition parameters being determined by its evaluation. When the thickness of the examination subject is additionally detected, the composition of the tissue (fat portion, gland portion, possibly-present micro-calcifications) of the examination subject can be derived for each image point (pixel) along the x-ray beam from the at least one intermediate image, that exhibits high resolution, and used as an additional criterion for the control of the acquisition parameter.

In a preferred embodiment of the method, the at least one acquisition parameter is determined dependent on an average intensity value in at least one predetermined area within the intermediate image, such as dependent on the thickness of the examination subject.

When the intermediate images acquired from preceding individual images are respectively evaluated, the acquisition parameters can be successively optimized.

The intermediate image can be evaluated to control the progression or the premature termination of the acquisition of the x-ray image. For example, in mammography suitable evaluation algorithms can establish whether the breast is correctly (i.e. corresponding to medical rules) positioned on the patient table. In exposures known as MLO exposures, for example, the pectoral muscle must be recognizable on the image up to the height of the nipple and appear convex. Artifacts (for example detector errors) can likewise already be established in the intermediate image and suggest a termination.

By comparing at least two intermediate images with one another, a determination can be made as to whether the acquisition of the x-ray image is continued or terminated. This case is, for example, when the examination subject is displaced (due to a patient movement) during an acquisition sequence.

The above cited object also is achieved by an apparatus for implementing the method described above.

DESCRIPTION OF THE DRAWINGS

FIG. 2 is a flowchart of an embodiment of the method according to the invention.

DESCRIPTION OF THE PREFERRED EMBODIMENTS

Figure 1:
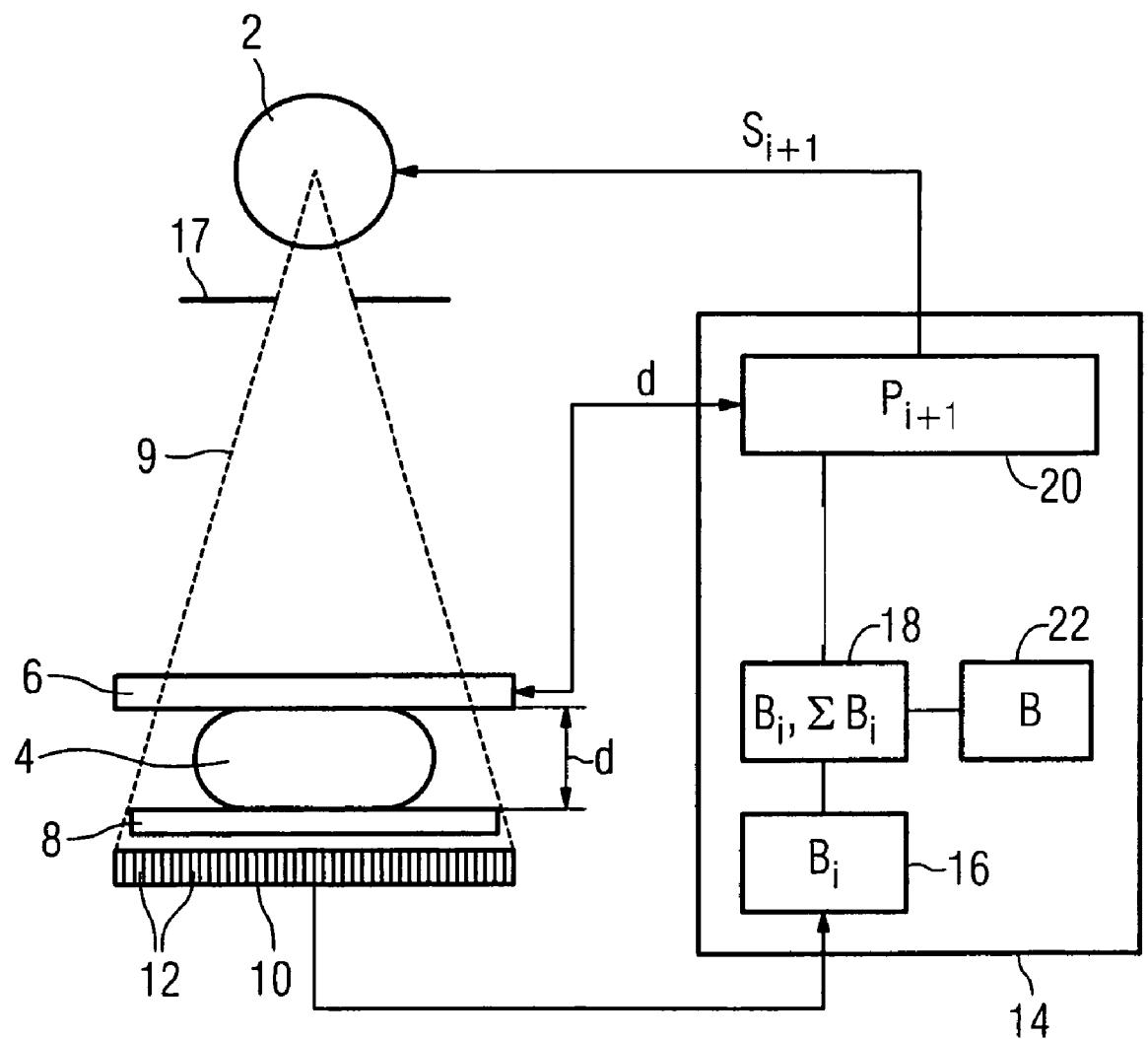
FIG. 1 schematically illustrates an apparatus according to the invention.

As shown in Figure, the apparatus (a mammography apparatus in the exemplary embodiment) has an x-ray tube 2 for generation of x-rays that traverse an examination subject 4. The examination subject 4 (a female breast in the exemplary embodiment) is embedded between a compression plate 6 and a support plate 8. The x-ray radiation 9 traversing the examination subject 4 and the plates 6 and 8 is received by a digital x-ray detector 10 that is formed by a number of individual detectors 12 arranged in a matrix-like array. The measurement signals of the individual detectors 12 are combined into a digital individual image $B_i$ with an image computer 16 in a control and evaluation device 14. In the exemplary embodiment, a situation is shown in which a diaphragm 17 delimits the image field acquired in the acquisition plane by the x-ray radiation 9 such that it fills the entire acquisition plane of the x-ray detector 10.

Using a number of successive individual shots, a number of individual images $B_i$ are acquired and stored and added in an image memory 18. Intermediate images $\Sigma B_i$ are formed (the sigma sign $\Sigma$ does not mean that an intermediate image $\Sigma B_i$ must necessarily be the sum of a number of individual images) from an individual image $B_i$ or via summation of a number of stored individual images $B_i$ and evaluated in an evaluation device 20, and the acquisition parameters $P_{i+1}$ suitable for the subsequent acquisition are determined and further processed into control signals $S_{i+1}$ with which the x-ray tube 2 is controlled.

Moreover, the intermediate images $\Sigma B_i$ are compared with one another in the evaluation device 20 in order to detect a displacement of the examination subject 4. If such a displacement is established, a termination of the acquisition sequence ensues. Otherwise, the acquisition sequence is continued and ended. After the end of the acquisition sequence, the individual images $B_i$ are combined into a finished, diagnostically-utilizable digital x-ray image B (end image) and reproduced in a reproduction device.

Moreover, for the image evaluation the thickness d of the examination subject (i.e, the separation of the compression plates 6 and 8) is detected and taken into account in the control and evaluation device 14.

As shown in FIG. 2, a first individual image $B_i=B_1$ is generated in a first step i=1 with a first preset parameter set $P_i=P_1$ with a dose that is significantly smaller than a dose normally required for a diagnostically-utilizable x-ray image and that is, for example, reduced by a factor of 10 relative to this dose. Using the intermediate image $\Sigma B_i=B_1$ composed of the first individual image $B_i=B_1$, the control signal $S_{i+1}=S_2$ as well as the acquisition parameters $P_{i+1}=P_2$ for the acquisition of the next individual image $B_{i+1}=B_2$ are now determined. At the same time, using the first acquired intermediate image $\Sigma B_i$ it is checked whether the examination subject is correctly positioned. In the case of an incorrect positioning (illustrated in the flow diagram by the value K=0 of a binary control signal K), a termination of the acquisition sequence ensues. Otherwise (K=1), the run index i is increased by 1 and the acquisition of the next individual image $B_{i+1}=B_2$ is effected with the newly determined parameter set $P_{i+1}=P_2$. This next individual image $B_2$ is compared With the intermediate image $\Sigma B_i=B_1$ formed by the preceding individual image $B_i$ or, for i>2, with preceding intermediate images $\Sigma B_i$ in order to establish a displacement of the examination subject. If such a displacement is detected, a termination of the acquisition sequence (K=0) ensues. For the case that a termination is indicated in none of the individual steps, this process is repeated until the run index i exceeds a predetermined number. In this manner, a number n of individual images $B_i$ with respectively-optimized acquisition parameters $P_i$ are successively acquired and combined in the end into the finished x-ray image $$B = \sum_{i=1}^{n} B_i.$$

Deviating from the method workflow shown in FIG. 2, in which a check and a re-determination of the acquisition parameters $P_i$ ensues after each individual image $B_i$, it is also possible to use the acquisition parameters $P_2$ determined after the first individual image $B_1$ for all successive acquisitions $B_2$ through $B_n$. As an alternative, a first acquisition sequence can also be implemented with constant acquisition parameters $P_2$ up to an m-th individual image $B_m$ (whereby m<n), and the acquisition parameters $P_{m+1}$ for the remaining individual images $B_{m+1}$-$B_n$ are determined from an intermediate image $B_1+B_2+\ldots+B_m$ formed from these individual images $B_1$-$B_m$. In other words: it is not absolutely necessary to re-determine the acquisition parameters $P_i$ using the preceding individual images $B_1, \ldots B_{i-1}$ before the acquisition of each individual image $B_i$. For example, given a pre-selected number n=10 of individual acquisitions, the individual images $B_2$-$B_5$ can thus all be implemented with the same acquisition parameters $P_2$ as they have been determined using the evaluation of the first individual image $B_1$. An intermediate image $\Sigma B_i$ formed by summation from the 5 individual images $B_1$-$B_5$ now present can now be adopted in order to determine the acquisition parameters $P_6$ (if applicable by additional evaluation of the thickness of the irradiated region) that are then used for the successive remainder of the individual acquisitions $B_6$-$B_{10}$.

Although modifications and changes may be suggested by those skilled in the art, it is the intention of the inventor to embody within the patent warranted hereon all changes and modifications as reasonably and properly come within the scope of his contribution to the art.

The invention claimed is:

1. A method for generating a digital x-ray image, comprising the steps of:

before producing a digital x-ray image of an examination subject from a plurality of individual images acquired in temporal succession with an x-ray source and a digital x-ray receiver, acquiring at least one of said plurality of individual images by activating said x-ray source and detecting radiation from said x-ray source, attenuated by said examination subject with said digital x-ray receiver;

forming at least one intermediate image from said at least one of said individual images;

automatically electronically evaluating said at least one intermediate image to obtain an evaluation result;

again activating said x-ray source and, with said digital x-ray receiver, acquiring a remainder of said plurality of individual images using at least one acquisition parameter that is controlled dependent on said evaluation result; and combining said plurality of individual images to produce said digital x-ray image of said examination subject with images in said plurality of individual images overlapping one another in at least one diagnostically relevant region of the examination subject represented in the digital x-ray image, and making said digital x-ray image available in displayable form.

2. A method as claimed in claim 1 comprising forming said at least one intermediate image from a first-acquired individual image of said at least one of said individual images.

3. A method as claimed in claim 1 comprising acquiring said remainder of said plurality of individual images with an exposure time, and controlling said exposure time, as said at least one acquisition parameter, dependent on said evaluation result.

4. A method as claimed in claim 1 wherein the step of evaluating said at least one intermediate image comprises evaluating said at least individual image to determine a thickness of the examination subject and a composition of tissue of the examination subject, and using said thickness and said composition of tissue as additional criterion for controlling the acquisition of said remainder of said plurality of individual images.

5. A method as claimed in claim 4 comprising acquiring said at least one of said plurality of individual images and acquiring said remainder of said plurality of individual images using an x-ray tube, having a tube operating parameter, as said x-ray source and controlling said tube operating parameter, as said at least one acquisition parameter, when acquiring said remainder of said plurality of individual images.

6. A method as claimed in claim 1 comprising automatically electronically determining, from said evaluation result, whether said remainder of said plurality of individual images should be acquired.

7. A method as claimed in claim 6 wherein the step of acquiring at least one of said plurality of individual images comprises acquiring two of said individual images, and wherein the step of forming at least one intermediate image comprises respectively forming two intermediate images from said two of said plurality of individual images, and wherein the step of automatically electronically determining, from said evaluation result, whether said remainder of said plurality of individual images should be acquired comprises automatically electronically comparing said two intermediate images with each other to obtain a comparison result, and automatically electronically using said comparison result to determine whether said remainder of said plurality of individual images should be acquired.

8. An apparatus for generating a digital x-ray image, comprising:
   an x-ray source that emits an x-ray beam;
   a digital x-ray receiver on which said x-ray beam is incident; and
   a control and imaging computer that operates said x-ray source and said x-ray receiver to acquire, before producing a digital x-ray image of an examination subject from a plurality of individual images acquired in temporal succession with a digital x-ray receiver, at least one of said plurality of individual images with said digital x-ray receiver, and to form at least one intermediate image from said at least one of said individual images, and to automatically electronically evaluate said at least one intermediate image to obtain an evaluation result, and to operate said x-ray source and said digital x-ray receiver, to acquire a remainder of said plurality of individual images using at least one acquisition parameter that is controlled dependent on said evaluation result, and to combine said plurality of individual images to form said digital x-ray image of said examination subject with images in said plurality of individual images overlapping one another in at least one diagnostically relevant region of the examination subject represented in the digital x-ray image.

9. An apparatus as claimed in claim 8 wherein said control and imaging computer form said at least one intermediate image from a first-acquired individual image of said at least one of said individual images.

10. An apparatus as claimed in claim 8 wherein said control and imaging computer operates said x-ray source and said x-ray receiver to acquire said remainder of said plurality of individual images with an exposure time, and controls said exposure time, as said at least one acquisition parameter, dependent on said evaluation result.

11. An apparatus as claimed in claim 8 wherein said control and imaging computer evaluates said at least one intermediate image to determine a thickness of the examination subject and a composition of tissue of the examination subject, and wherein said control and imaging computer operates said x-ray source and said x-ray receiver to acquire said remainder of said plurality of individual images using said thickness and said composition of tissue as additional criterion for controlling the acquisition of said remainder of said plurality of individual images.

12. An apparatus as claimed in claim 11 wherein said x-ray source is an x-ray tube having a tube operating parameter, and wherein said control and imaging computer controls said tube operating parameter, as said at least one acquisition parameter, when acquiring said remainder of said plurality of individual images.

13. An apparatus as claimed in claim 8 wherein said control and imaging computer automatically electronically determines, from said evaluation result, whether said remainder of said plurality of individual images should be acquired.

14. An apparatus as claimed in claim 13 wherein said control and imaging computer operates said x-ray source and said x-ray receiver to acquire at least one of said plurality of individual images by acquiring two of said individual images, and wherein said control and imaging computer forms at least one intermediate image by respectively forming two intermediate images from said two of said plurality of individual images, and wherein said control and imaging computer automatically electronically determines, from said evaluation result, whether said remainder of said plurality of individual images should be acquired by automatically electronically comparing said two intermediate images with each other to obtain a comparison result, and automatically electronically using said comparison result to determine whether said remainder of said plurality of individual images should be acquired.

* * * * *